United States Patent [19]

Seiler, Jr.

[11] 4,393,699
[45] Jul. 19, 1983

[54] PNEUMATIC ADHESION TESTER

[75] Inventor: James F. N. Seiler, Jr., Frederick, Md.

[73] Assignee: The United States of America as represented by the Secretary of Commerce, Washington, D.C.

[21] Appl. No.: 272,231

[22] Filed: Jun. 11, 1981

[51] Int. Cl.³ .............................................. G01N 19/08
[52] U.S. Cl. .................... 73/150 A; 73/37; 73/827
[58] Field of Search .......... 73/37, 827, 150 A, 150 R; 33/169 F; 269/22

[56] References Cited

U.S. PATENT DOCUMENTS 2,167,652  8/1939  Hoch ................................. 33/169 F
3,433,699  3/1969  Rumble ................................. 269/22
3,821,892  7/1974  Säberg ............................. 73/150 A

FOREIGN PATENT DOCUMENTS 1455534  11/1976  United Kingdom ............ 73/150 A

Primary Examiner—E. R. Kazenske
Assistant Examiner—Denis E. Corr
Attorney, Agent, or Firm—Eugene J. Pawlikowski; Alvin J. Englert

[57] ABSTRACT

This tester comprises a fixture which is bonded to a coating or surface, and a plate and a membrane which are sealed together along their peripheries. A hole extends through the membrane and at least into the plate for receiving the fixture so that its bonding surface is flush with the membrane. The plate has a gas opening which is connectable with a source of pressurized gas.

4 Claims, 11 Drawing Figures

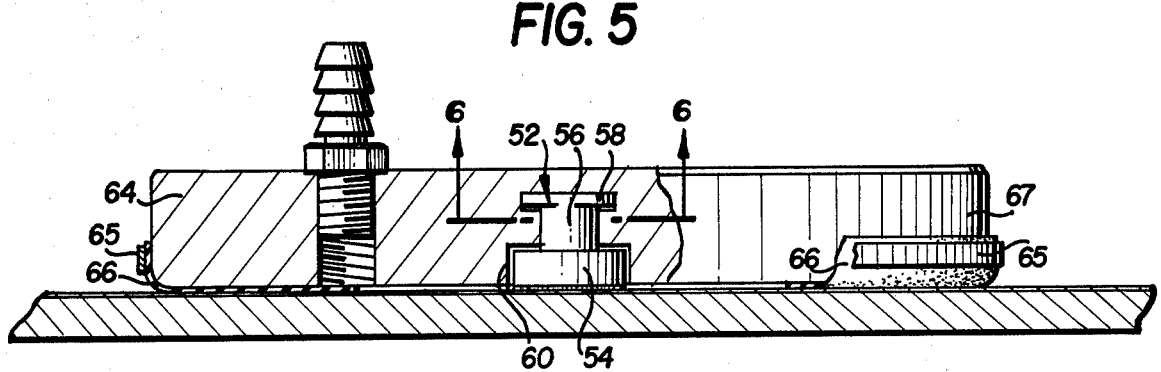
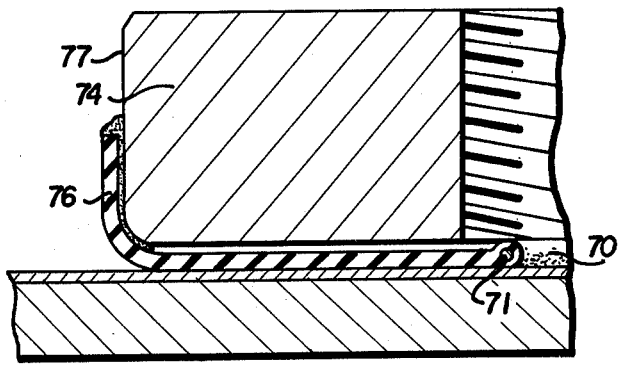
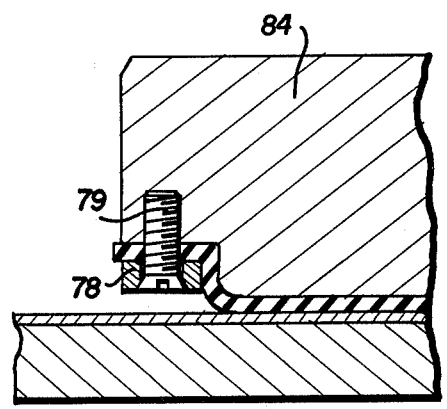
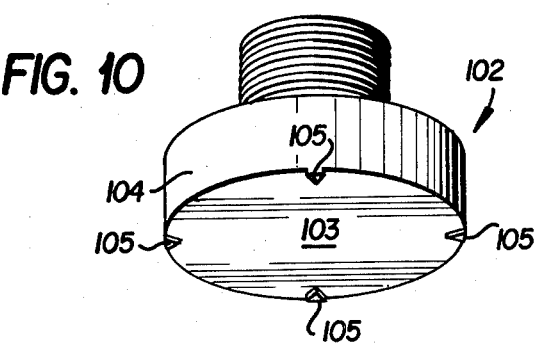
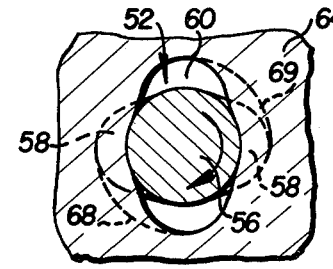
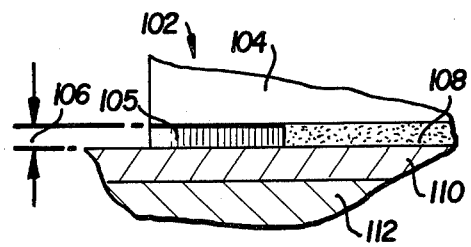
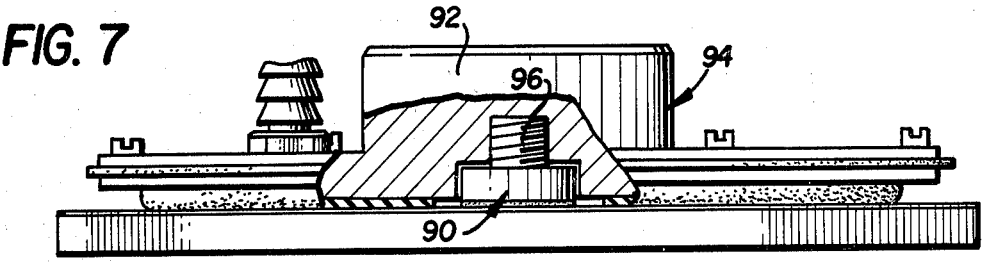

PNEUMATIC ADHESION TESTER

Adhesion testers are devices that measure the bond strength of coatings (paints, varnishes, etc.) or adhesives. They include a fixture that is bonded to the coating with a high-strength adhesive (epoxy for example), or to a clean surface if the adhesive itself is to be tested. The fixture is then coupled to a mechanical, pneumatic, or hydraulic puller that pulls the fixture until the coating or adhesive under test separates from the surface. The force required for separation provides a measure of the bond strength.

Hand-operated mechanical testers generally apply the pulling force intermittently, which reduces the reproducibility of the results. Pneumatic or hydraulic testers apply the pulling force at a uniform rate, but the devices tend to be bulky and heavy and thus tend to subject the fixture to tipping or twisting torques that introduce errors into the measurement.

The present tester is pneumatic and therefore capable of loading the fixture at a uniform, controlled rate. The tester is also light and compact to minimize the possibility of applying forces other than tensile pull to the fixture. The tester comprises a plate and a membrane which are sealed together along their peripheries. A hole extends through the membrane and into or through the plate for receiving the fixture so that its bonding surface is substantially flush with the membrane. The plate has a gas inlet which is connectable to a source of pressurized air, nitrogen or other gas. In operation, the membrane and plate are placed over and secured to the fixture and gas is introduced between the membrane and plate. The gas presses the membrane into gas-tight contact with the surface to which the fixture is bonded and then forces the membrane and plate apart until the fixture is pulled from the surface. The compliancy of the membrane minimizes the application of non-tensile forces to the fixture.

FIG. 1 of the drawings is a plan view of the tester;

FIGS. 5 and 7 are partly sectioned elevation views of two other testers;

FIG. 6 is a sectional view taken on line 6—6 of FIG. 5;

FIGS. 8 and 9 are sectional views of other plate and membrane seals;

FIG. 10 is a perspective view of the fixture; and

FIG. 11 is a partly sectioned elevation view of the fixture, adhesive, coating and substrate.

Figure 1:
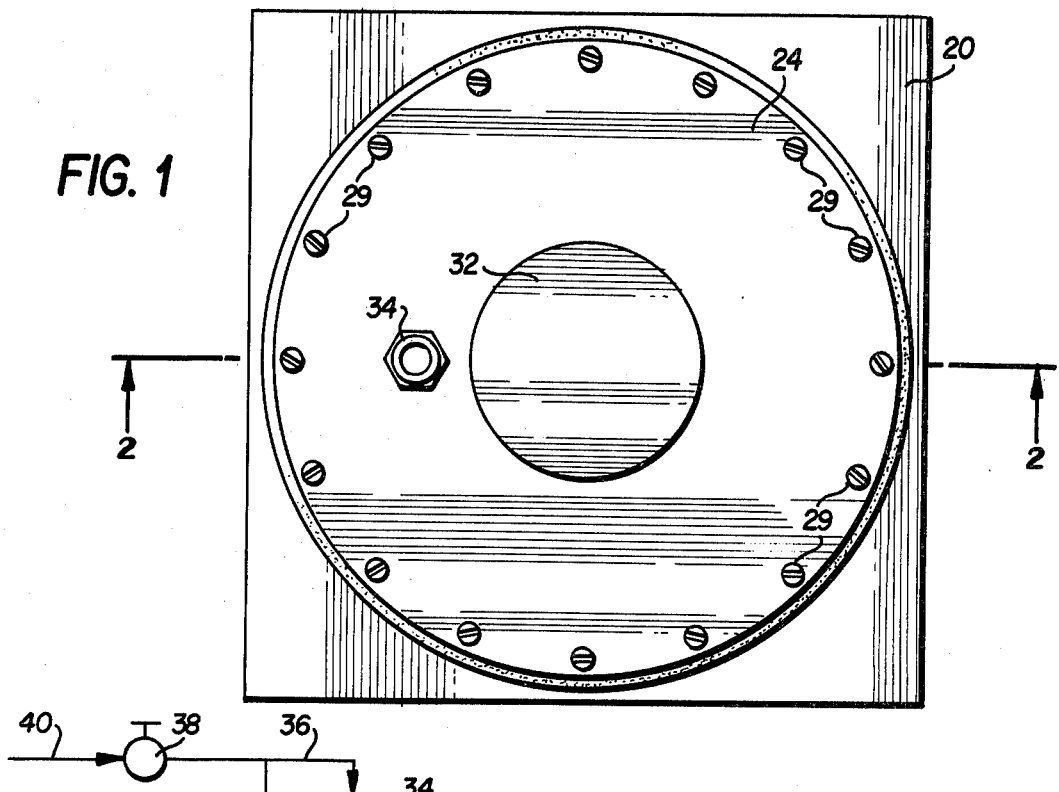
Figure 2:
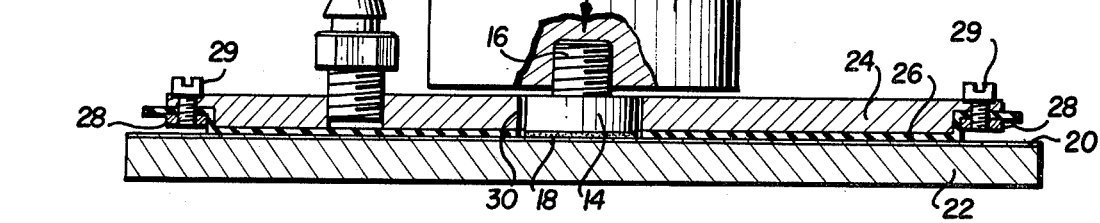
FIG. 2 is a sectional view taken on line 2—2 of FIG. 1.

As shown in FIGS. 1–4, the adhesion tester includes a fixture 12 which conveniently is bolt-like with a head 14 and shank 16. The head 14 is shown bonded by a layer of adhesive 18 to a coating 20 on a substrate 22. To test the adhesive 18, the head 14 would be bonded to an uncoated substrate (not shown).

The tester further includes a circular plate 24 and a membrane 26 which are sealed along their peripheries by a ring 28 and screws 29. The peripheral edge of the plate 24 is recessed to receive the ring 28. The membrane 26 and plate 24 have a hole 30 for receiving the fixture 12 so that its head 14 is substantially flush with the membrane 26. The plate 24 is secured to the fixture 12 by a cap 32 which may, for example, be screwed onto threads provided on the shank 16 of the fixture 12. The plate 24 is provided with a gas inlet 34 which is connected by a flexible line 36 and valve 38 to a pressurized gas source 40. The gas pressure is measured by a pressure gage and recorder 42.

Figure 3:
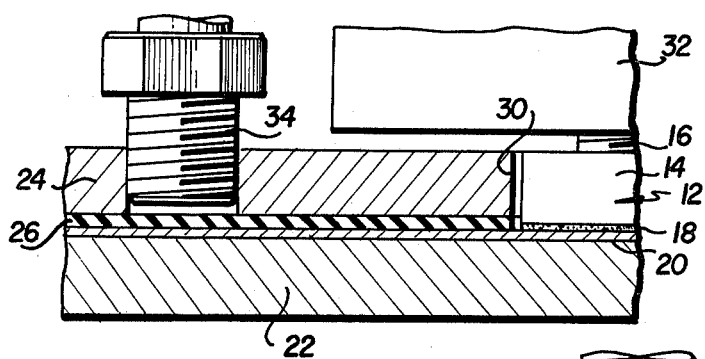
FIGS. 3 and 4 are enlarged views of part of FIG. 2.
Figure 4:
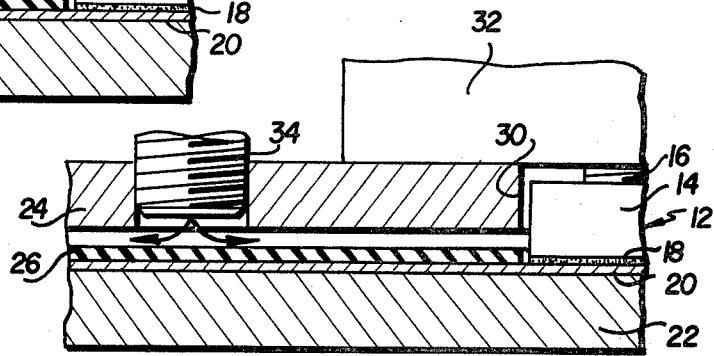

In operation, the fixture 12 is bonded to the coating 20, and the plate 24 and membrane 26 are placed on the fixture 12 so that the membrane 26 is substantially flush with the head 14 and coating 20. The cap 32 is screwed onto the shank 16 until it is near but preferably not touching the plate 24. The flexible line 36 is connected to the gas inlet 34 and the valve 38 is slowly opened to allow the pressurized gas (air or if necessary an inert or other special gas such as nitrogen) to flow between the plate 24 and membrane 26. The gas presses the membrane 26 down into gas-tight contact with the coating 20 and presses the plate 24 up into gas-tight contact with the cap 32. FIGS. 3 and 4 illustrate the positions of the plate 24 before and after pressurization. With the hole 30 in the plate 24 and membrane 26 thus sealed, the pressurized gas forces the plate 24 and membrane 26 apart until the coating 20 bonded to the head 14 of fixture 12 separates from the substrate 22. The valve 38 is then closed and the cap 32 is unscrewed from the fixture 12. The torn-off portion of coating 20 and adhesive layer 18 are then removed from the fixture 12 so that it may be re-used.

The pressure required to achieve separation is observed and preferably recorded and used to determine, via a calibration curve, the bond strength of the coating 20.

The membrane 26 is a pliant, gas-impervious material such as rubber, polymer or thin metal. The compliancy of the membrane 26 minimizes the application to the fixture 12 of non-tensile forces that would otherwise cause the coating 20 to separate at erroneously low gas pressures.

FIGS. 5 and 6 illustrate an alternate fixture 52 which has a head 54, shank 56, and an oval key 58. The plate 64 has an opening 60 which extends into but not through the plate. The opening 60 is oval, as shown in FIG. 6, to permit the oval key 58 to enter the plate 64 and engage shoulders 68, 69 when the plate 64 is rotated a quarter turn. This construction eliminates the need for the cap 32 shown in FIGS. 1 and 2.

FIG. 5 also illustrates an alternate method for sealing the plate 64 and membrane 66 together along their peripheries, comprising a tensioned metal band 65 that clamps the membrane 66 to the cylindrical surface 67 of the plate 64. FIG. 8 shows a membrane 76 that is adhesively bonded to the cylindrical surface 77 of a plate 74. The membrane 76 has a relatively large hole 70 that is reinforced by a wire bead 71. FIG. 9 illustrates the use of a ring 78 similar to the ring 28 of FIG. 2 with screws 79 that thread into tapped holes provided in the recessed peripheral edge of the plate 84.

FIG. 7 illustrates a plate 94 with an integral cap portion 92. The cap portion 92 has a tapped hole so that the integral cap 92 and plate 94 can be threaded onto the shank 96 of the fixture 90.

FIGS. 10 and 11 illustrate a fixture 102 in which the bonding surface 103 of the head 104 has been recessed as by milling to leave at least three small projections 105. The projections 105 control the thickness 106 of the adhesive layer 108 when the fixture 102 and wet adhesive 108 are pressed onto a coating 110 on a substrate 112. The projections 105 thus aid in providing a reproducible adhesive layer 108.

I claim:

1. A pneumatic adhesion tester comprising:

a fixture having a bonding surface adapted to be bonded to a coated or uncoated substrate, a plate and a membrane sealed together solely along their outer peripheries, said membrane being adapted to directly contact said coated or uncoated substrate, a hole extending through said membrane and at least into said plate for receiving said fixture so that said bonding surface is substantially flush with said membrane, means for introducing a pressurized gas between said plate and membrane, said membrane having said hole being adapted to be thereby pressed into gas-tight contact with said coated or uncoated substrate, said bonding surface remaining flush with said membrane until the bonding surface separates, and means for measuring the pressure of said gas introduced between said plate and membrane.

2. A tester as set forth in claim 1 wherein said hole and said fixture extend through said plate and means are provided for securing said fixture to said plate.

3. A tester as set forth in claim 1 wherein said bonding surface has at least three small projections for establishing a uniform thickness of adhesive between said bonding surface and a test surface.

4. A tester as set forth in claim 1 wherein said gas introducing means includes a valve.

* * * * *